US009643133B2

(12) United States Patent
Goodwin et al.

(10) Patent No.: US 9,643,133 B2
(45) Date of Patent: May 9, 2017

(54) CONTAINER WITH FILM SPARGER

(71) Applicant: HyClone Laboratories, Inc., Logan, UT (US)

(72) Inventors: Michael E. Goodwin, Logan, UT (US); Nephi D. Jones, Newton, UT (US); Derik R. West, Logan, UT (US)

(73) Assignee: Life Technologies Corporation, Carlsbad, CA (US)

( * ) Notice: Subject to any disclaimer, the term of this patent is extended or adjusted under 35 U.S.C. 154(b) by 239 days.

(21) Appl. No.: 13/631,448

(22) Filed: Sep. 28, 2012

(65) Prior Publication Data

US 2013/0082410 A1  Apr. 4, 2013

Related U.S. Application Data

(60) Provisional application No. 61/541,913, filed on Sep. 30, 2011.

(51) Int. Cl.
*B01F 3/04* (2006.01)
*B01F 15/00* (2006.01)
*C12M 1/00* (2006.01)

(52) U.S. Cl.
CPC ...... *B01F 3/04269* (2013.01); *B01F 15/0085* (2013.01); *C12M 23/14* (2013.01);
(Continued)

(58) Field of Classification Search
CPC  B01F 3/04269; B01F 5/0085; B01F 15/0085; B01F 2003/04148;
(Continued)

(56) References Cited

U.S. PATENT DOCUMENTS 1,269,189 A   6/1918  Kadish
1,471,332 A  10/1923  Greenawalt
(Continued)

FOREIGN PATENT DOCUMENTS

CA   2214384       10/1996
CH    675368 A5    9/1990
(Continued)

OTHER PUBLICATIONS

U.S. Appl. No. 60/577,143, filed Jun. 4, 2004 to Hodge.
(Continued)

*Primary Examiner* — Amber R Orlando
*Assistant Examiner* — Stephen Hobson
(74) *Attorney, Agent, or Firm* — Workman Nydegger

(57) ABSTRACT

A container assembly includes a flexible bag having an interior surface bounding a chamber and an opposing exterior surface, the bag having a top end wall, a bottom end wall, and an encircling sidewall extending therebetween, the bottom end wall including a first polymeric sheet overlying a second polymeric sheet. A first weld line welds the first polymeric sheet to the second polymeric sheet, the first weld line bounding a first sparging area formed between the first polymeric sheet and the second polymeric sheet. A plurality of first perforations are formed through a portion of the first polymeric sheet that overlies the first sparging area so that gas can pass from the first sparging area, through the first perforations and into the chamber of the bag.

32 Claims, 11 Drawing Sheets

(52) U.S. Cl.
CPC ............ *C12M 23/26* (2013.01); *C12M 23/40* (2013.01); *C12M 29/06* (2013.01); *B01F 2003/04148* (2013.01); *B01F 2003/04191* (2013.01); *B01F 2003/04297* (2013.01); *B01F 2003/04326* (2013.01); *B01F 2003/04347* (2013.01); *B01F 2003/04361* (2013.01)

(58) Field of Classification Search
CPC .. B01F 2003/04297; B01F 2003/04326; B01F 2003/04361; B01F 2003/04347; B01F 2003/04191; C12M 23/26; C12M 23/40; C12M 29/06; C12M 23/14
USPC ...................................................... 261/122.1
See application file for complete search history.

(56) References Cited

U.S. PATENT DOCUMENTS

| | | | |
|---|---|---|---|
| 1,505,204 | A | 8/1924 | Kiernan |
| 2,259,243 | A | 10/1941 | Daman |
| 2,341,114 | A * | 2/1944 | Novak ................... A61M 5/165 210/448 |
| 2,865,618 | A | 12/1958 | Abell |
| 3,184,395 | A | 5/1965 | Brewer |
| 3,647,397 | A | 3/1972 | Coleman |
| 3,682,168 | A | 8/1972 | Deaton |
| 3,701,433 | A * | 10/1972 | Krakauer ............... A61M 1/3627 210/436 |
| 3,702,619 | A * | 11/1972 | Son ....................... B01F 5/0456 137/3 |
| 3,796,417 | A | 3/1974 | Kaelin |
| 4,012,471 | A | 3/1977 | Kunkle, Jr. |
| 4,012,473 | A | 3/1977 | Lindsey et al. |
| 4,025,590 | A | 5/1977 | Igich |
| 4,036,919 | A | 7/1977 | Komendowski et al. |
| 4,061,698 | A | 12/1977 | Thornwald |
| 4,100,235 | A | 7/1978 | Thornwald |
| 4,157,965 | A * | 6/1979 | Raible ................. A61M 1/3627 210/305 |
| 4,204,774 | A | 5/1980 | de Bruyne |
| 4,250,039 | A * | 2/1981 | Cozzi ................... B01D 29/111 210/416.5 |
| 4,391,912 | A * | 7/1983 | Yoshida ................. C12M 29/16 435/297.4 |
| 4,465,645 | A | 8/1984 | Kaelin |
| 4,493,637 | A | 1/1985 | Ganter et al. |
| 4,581,143 | A * | 4/1986 | Pepper, III ................ C02F 3/06 210/614 |
| 4,668,632 | A | 5/1987 | Young et al. |
| 4,684,486 | A | 8/1987 | Ricchio |
| 4,727,040 | A | 2/1988 | Freedman et al. |
| 4,740,202 | A | 4/1988 | Stacey et al. |
| 4,749,654 | A | 6/1988 | Karrer et al. |
| 4,814,124 | A | 3/1989 | Aoyama et al. |
| 4,869,852 | A | 9/1989 | Goudy, Jr. et al. |
| 4,981,623 | A | 1/1991 | Ryan |
| 5,008,197 | A | 4/1991 | Wergeland et al. |
| 5,057,429 | A | 10/1991 | Watanabe et al. |
| 5,183,595 | A | 2/1993 | Schüssler |
| RE34,386 | E | 9/1993 | Davidson et al. |
| 5,270,207 | A | 12/1993 | Matsumura et al. |
| 5,376,271 | A | 12/1994 | Morgan, Jr. |
| 5,416,022 | A * | 5/1995 | Amiot ................... B01D 63/00 435/297.2 |
| 5,422,043 | A | 6/1995 | Burris |
| 5,443,985 | A | 8/1995 | Lu et al. |
| 5,458,771 | A | 10/1995 | Todd |
| 5,565,015 | A * | 10/1996 | Kobayashi ................ C05F 9/04 435/290.1 |
| 5,578,459 | A | 11/1996 | Gordon |
| 5,693,537 | A | 12/1997 | Wilson et al. |
| 5,763,267 | A * | 6/1998 | Kurjan ................... C12M 23/26 435/293.1 |
| 5,799,830 | A | 9/1998 | Carroll et al. |
| 5,858,283 | A | 1/1999 | Burris |
| 5,897,997 | A | 4/1999 | Louvel |
| 5,925,293 | A * | 7/1999 | Howk ................. B01F 3/04248 261/123 |
| 5,941,635 | A | 8/1999 | Stewart |
| 6,071,005 | A | 6/2000 | Ekambaram et al. |
| 6,083,587 | A | 7/2000 | Smith et al. |
| 6,086,574 | A | 7/2000 | Carroll et al. |
| 6,117,801 | A | 9/2000 | McGinty et al. |
| 6,146,875 | A * | 11/2000 | Ward ..................... C12M 23/14 383/104 |
| 6,186,932 | B1 | 2/2001 | Vallot |
| 6,219,871 | B1 | 4/2001 | Frederick et al. |
| 6,245,555 | B1 | 6/2001 | Curtis |
| 6,250,796 | B1 | 6/2001 | Huang |
| H1989 | H | 9/2001 | Fell et al. |
| 6,367,783 | B1 * | 4/2002 | Raftis ................. B01F 3/04269 261/122.1 |
| 6,391,638 | B1 | 5/2002 | Shaaltiel |
| 6,398,195 | B1 | 6/2002 | Sherman |
| 6,406,005 | B1 | 6/2002 | Lawson et al. |
| 6,432,698 | B1 * | 8/2002 | Gaugler ................. C12M 23/14 435/296.1 |
| 6,439,756 | B1 | 8/2002 | Forschner et al. |
| 6,464,211 | B1 | 10/2002 | Downs |
| 6,468,792 | B1 | 10/2002 | Bader |
| 6,494,613 | B2 | 12/2002 | Terentiev |
| 6,518,057 | B2 * | 2/2003 | Morrison ............. C05F 17/0205 435/290.1 |
| 6,632,658 | B1 * | 10/2003 | Schoeb ................. C12M 21/08 435/1.2 |
| 6,649,405 | B2 | 11/2003 | Alms et al. |
| 6,670,169 | B1 | 12/2003 | Schöb et al. |
| 6,673,598 | B1 | 1/2004 | Akers et al. |
| 6,709,862 | B2 | 3/2004 | Curtis |
| 6,712,963 | B2 * | 3/2004 | Schick ................. A61M 1/0209 210/137 |
| 6,884,866 | B2 | 4/2005 | Bronshtein et al. |
| 6,923,567 | B2 | 8/2005 | Bibbo et al. |
| 7,141,203 | B2 | 11/2006 | Way et al. |
| 7,198,255 | B2 | 4/2007 | Chiba |
| 7,278,780 | B2 | 10/2007 | Goodwin et al. |
| 7,326,355 | B2 | 2/2008 | Graetz et al. |
| 7,384,027 | B2 | 6/2008 | Terentiev et al. |
| 7,384,783 | B2 | 6/2008 | Kunas et al. |
| 7,431,837 | B2 | 10/2008 | Cohee et al. |
| 7,448,601 | B2 * | 11/2008 | Boer ....................... B01J 8/1818 261/121.1 |
| 7,469,884 | B2 | 12/2008 | Terentiev et al. |
| 7,629,167 | B2 | 12/2009 | Hodge et al. |
| 7,681,867 | B2 | 3/2010 | Hu et al. |
| 7,682,067 | B2 | 3/2010 | West et al. |
| 7,879,599 | B2 * | 2/2011 | Goodwin ................. C12M 23/14 435/289.1 |
| 8,282,267 | B2 * | 10/2012 | Castillo ................. B01F 3/1221 366/262 |
| 8,603,805 | B2 | 12/2013 | Goodwin et al. |
| 8,960,486 | B2 * | 2/2015 | Goodwin ............. B01F 7/00691 220/661 |
| 9,005,971 | B2 | 4/2015 | Goodwin et al. |
| 2002/0063347 | A1 | 5/2002 | Lee et al. |
| 2002/0131654 | A1 | 9/2002 | Smith et al. |
| 2003/0077466 | A1 | 4/2003 | Smith et al. |
| 2003/0119185 | A1 | 6/2003 | Berenson et al. |
| 2004/0062140 | A1 | 4/2004 | Cadogan et al. |
| 2004/0095842 | A1 | 5/2004 | Weetman |
| 2005/0158851 | A1 | 7/2005 | Furey |
| 2005/0218075 | A1 | 10/2005 | Graetz et al. |
| 2005/0239199 | A1 | 10/2005 | Kunas et al. |
| 2005/0272146 | A1 | 12/2005 | Hodge et al. |
| 2005/0282269 | A1 * | 12/2005 | Proulx ................... C12M 23/02 435/296.1 |
| 2006/0054557 | A1 | 3/2006 | Hori et al. |
| 2006/0196501 | A1 | 9/2006 | Bibbo et al. |
| 2006/0270036 | A1 * | 11/2006 | Goodwin ............. B01F 3/04269 435/395 |
| 2008/0068920 | A1 * | 3/2008 | Galliher ............. B01F 3/04106 366/102 |

(56) References Cited

U.S. PATENT DOCUMENTS

| | | | |
|---|---|---|---|
| 2008/0139865 A1 | 6/2008 | Galliher | |
| 2008/0293133 A1 | 11/2008 | Reid et al. | |
| 2009/0035856 A1 | 2/2009 | Galliher et al. | |
| 2010/0078395 A1 | 4/2010 | Shevitz | |
| 2010/0174099 A1* | 7/2010 | Behkish | B01J 8/006 |
| | | | 549/518 |
| 2011/0020922 A1 | 1/2011 | Wuenn et al. | |
| 2012/0238011 A1 | 9/2012 | Tuohey et al. | |
| 2012/0313267 A1* | 12/2012 | Pradel | B01F 3/04262 |
| | | | 261/124 |
| 2015/0118753 A1* | 4/2015 | Brau | B01F 13/0272 |
| | | | 435/394 |
| 2016/0244710 A1* | 8/2016 | Wood | B01F 7/22 |

FOREIGN PATENT DOCUMENTS

| | | |
|---|---|---|
| DE | 200 07 347 U1 | 8/2000 |
| DE | 202010013812 U1 * | 2/2011 |
| EP | 0 343 885 | 11/1989 |
| EP | 1 602 715 A3 | 12/2005 |
| FR | 2 519 020 | 1/1983 |
| FR | 2 799 138 | 4/2001 |
| GB | 2 202 549 A | 9/1988 |
| JP | 50-119561 | 9/1975 |
| JP | 58-224683 | 12/1983 |
| JP | 61-067476 | 4/1986 |
| JP | 62-160899 | 7/1987 |
| JP | S6384483 A | 4/1988 |
| JP | 2-31825 | 2/1990 |
| JP | 02-283274 | 11/1990 |
| JP | 03-010675 | 1/1991 |
| JP | 03-242297 | 10/1991 |
| JP | 05-336957 | 12/1993 |
| JP | 06-153902 | 6/1994 |
| JP | 70-08264 | 1/1995 |
| JP | 07-155170 | 6/1995 |
| JP | 82-24076 | 9/1996 |
| JP | 10-099071 | 4/1998 |
| JP | 10-150972 | 9/1998 |
| JP | 10-313718 | 12/1998 |
| JP | 11-502716 | 3/1999 |
| JP | 11-299478 | 11/1999 |
| JP | 2001-258547 | 9/2001 |
| JP | 2002-101867 | 4/2002 |
| JP | 2007-511230 | 5/2007 |
| RU | 2 220 917 C1 | 1/2004 |
| WO | 96/30497 | 10/1996 |
| WO | 01/25394 | 4/2001 |
| WO | 02/41484 A2 | 5/2002 |
| WO | 2005/068059 A1 | 7/2005 |
| WO | 2005/118771 | 12/2005 |
| WO | 2006/116067 A1 | 11/2006 |
| WO | 2007/134267 A2 | 11/2007 |
| WO | 2008/040568 A1 | 4/2008 |
| WO | WO 2008157181 A1 * | 12/2008 ............. B01F 11/04 |
| WO | 2011/025890 A1 | 3/2011 |
| WO | 2013/049692 A1 | 4/2013 |

OTHER PUBLICATIONS

DuPont Medical Packaging, Technical Reference Guide for Medical Packaging, The Miracles of Science, 2002.

International Search Report and Written Opinion dated Jan. 17, 2013, issued in PCT/US2012/058086, filed Sep. 28, 2012.

Supplementary European Search Report dated Oct. 15, 2012 issued in EP Application No. 06750951.3, filed Apr. 21, 2006.

* cited by examiner

US 9,643,133 B2

CONTAINER WITH FILM SPARGER

CROSS-REFERENCE TO RELATED APPLICATIONS

This application claims benefit to Provisional Application No. 61/541,913, filed Sep. 30, 2011, which is incorporated herein by specific reference.

BACKGROUND OF THE INVENTION

1. The Field of the Invention

The present invention relates to spargers incorporated into a flexible bag.

2. The Relevant Technology

Spargers are commonly used in bioreactors for delivering controlled volumes of gas to a growth media containing cells. In part, the gas is used to control the partial pressure of oxygen within the growth media and to control the pH and other perimeters of the growth media so that the conditions are optimal for cell growth. Spargers typically comprise a hollow metal ring having a hose coupled thereto. The ring is formed from a sintered metal so that the ring is porous. The ring is manually positioned at the bottom of a container with the hose extending up through a port at the top of the container. During operation, pressurized gas is delivered to the ring through the hose. The gas then permeates out through the metal ring so as to enter the media in the form of small bubbles. As the bubbles travel up through the media, at least a portion of the gas becomes entrained within the media. Other conventional spargers comprise a section of stainless steel tubing that is bent into a ring with small diameter holes positioned along the curved length thereof Although conventional spargers are useful in delivering gas to the media, they have a number of shortcomings. For example, conventional spargers are relatively expensive to make and are thus designed to be reused. Reuse of a conventional sparger, however, requires that it be removed from the container and then cleaned and sterilized. In some situations, cleaning of the sparger can be difficult in that cell by-product, dead cells, and other particulate within the growth media can be lodged on or trapped within the sparger. Thus cleaning and sterilizing of the sparger can be both time consuming and expensive. Time and care must also be taken to properly position and seal the sparger within the container without contaminating the sparger or the container.

Furthermore, in conventional bioreactors it is necessary that the growth media containing the cells be continually mixed or suspended so that the properties of the growth media remain homogeneous. Conventional spargers can obstruct the flow of the fluid which can produce dead spots where the cells die. Furthermore, the cells can be caught on or by the sparger which can damage or kill the cells. In addition, the spargers must be carefully designed and positioned so that they do not obstruct the mixing system.

Some current bioreactors comprise a flexible bag that is disposed within a rigid support housing. The cell culture is grown within the sterile compartment of the flexible bag. In an attempt to eliminate some of the above sparger problems, disposable spargers have been incorporated into the flexible bags. Such disposable spargers comprise a port having an enlarged annular flange welded to the inside of the bag and a tubular stem that projects from the flange to outside the bag. The stem bounds a passage that extends through the flange. A porous film overlays the flange inside of the bag so as to cover the passage and is welded around the perimeter edge of the flange. As a result, gas can be passed through the stem from outside the bag. The gas passes through the flange and then passes through the porous film where it enters the cell culture within the bag in the form of small bubbles. When the cell production is completed, the bag and associated sparger are simply disposed of.

Although the above flexible sparger eliminates some of the problems of conventional spargers, the new bag spargers also have their shortcomings. Most notably, the bag spargers only sparge at a relatively small, fixed location on the bag and are limited to only one size of gas bubbles. As such, bag spargers have limited or no adjustability with regard to sparging at different locations, flow rates, bubbles sizes, or combinations of the forgoing.

Accordingly, what is needed are spargers and container systems that can solve one or more of the above shortcomings.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

The present invention relates to film spargers as well as container systems that incorporate such spargers. In general, one embodiment of a film sparger comprises overlying sheets of flexible material wherein one or more weld lines weld the sheets together so that a sparging area is bounded between the overlying sheets. A gas line is in communication with the sparging area for delivering a gas thereto while perforations are formed through one of the sheets so that gas passing into the sparging area can pass out through the perforations for sparging a fluid. Film spargers are typically incorporated into a flexible bag or other type of container for sparging a fluid within the container or for otherwise delivering gas bubbles to the fluid within the container.

Figure 1:
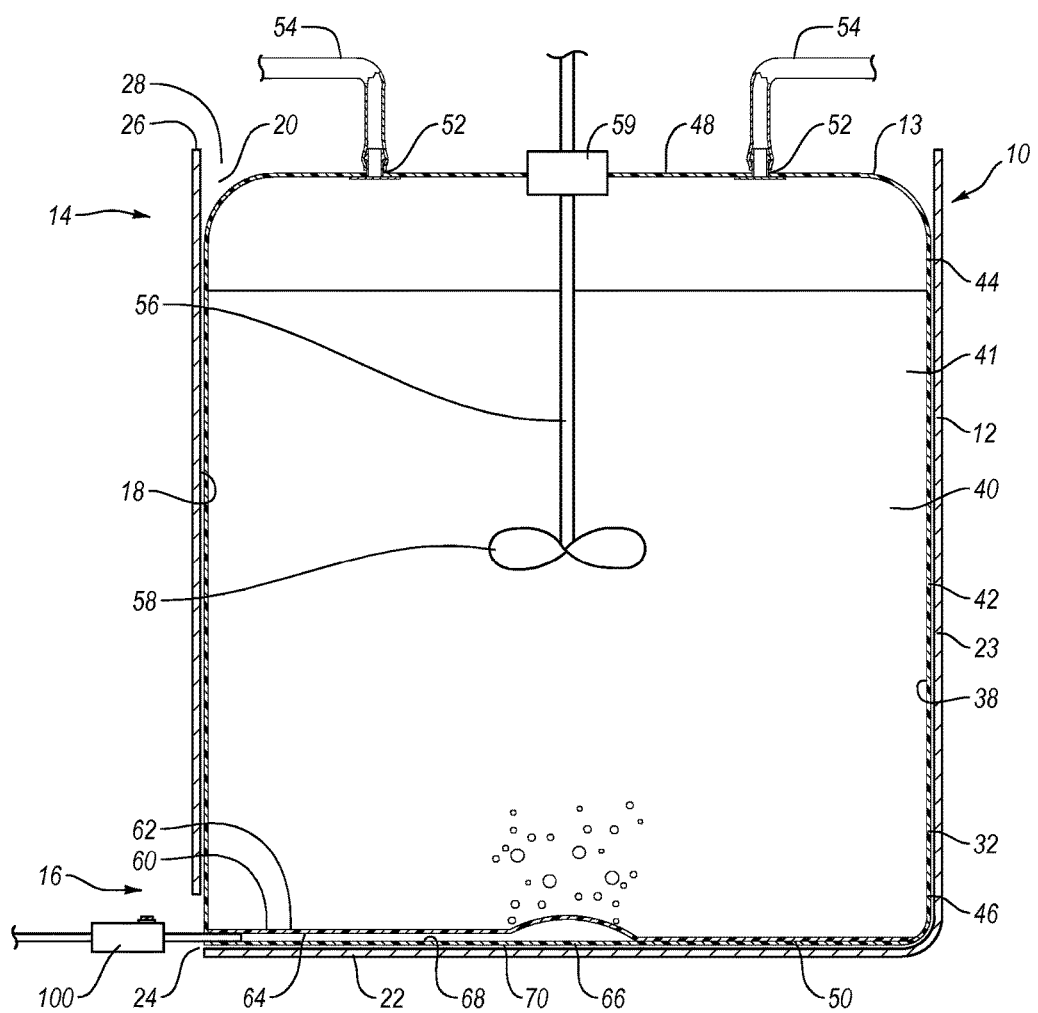
FIG. 1 is a cross section view of one embodiment of a container assembly within a support housing, a container assembly incorporating a sparger.

Depicted in FIG. 1 is one embodiment of a containment system 10 incorporating features of the present invention. Containment system 10 comprises a substantially rigid support housing 12 in which a container assembly 13 is disposed. Support housing 12 has an upper end 14, a lower end 16, and an interior surface 18 that bounds a compartment 20. Formed at lower end 16 is a floor 22. An encircling sidewall 23 extends up from floor 22 toward upper end 14. As will be discussed below in greater detail, one or more openings 24 can extend through floor 22 or sidewall 23 of support housing 12 so as to communicate with compartment 20. Upper end 14 terminates at a lip 26 that bounds an inlet opening 28 to compartment 20. If desired, a cover, not shown, can be mounted on upper end 14 so as to cover inlet opening 28. Likewise, an access opening can be formed at another location on support housing 12 such as through sidewall 23 at second end 16 or through floor 22. The access opening is large enough so that an operator can reach through the access opening to help manipulate and position container assembly 13. The access opening can be selectively closed by a door or cover plate.

It is appreciated that support housing 12 can come in a variety of different sizes, shapes, and configurations. For example, floor 22 can be flat, frustoconical, or have other slopes. Sidewall 23 can have a transverse cross section that is circular, polygonal or have other configurations. Support housing 24 can be insulated and/or jacketed so that a heated or cooled fluid can flow through the jacket for heating or cooling the fluid contained within container assembly 13. Compartment 20 can be any desired volume such as those discussed below with regard to container 32.

As also depicted in FIG. 1, container assembly 13 is at least partially disposed within compartment 20 of support housing 12. Container assembly 13 comprises a container 32 having one or more ports 52 mounted thereon. In the embodiment depicted, container 32 comprises a flexible bag having an interior surface 38 that bounds a chamber 40 suitable for holding a fluid 41 or other type of material. More specifically, container 32 comprises a side wall 42 that, when container 32 is inflated, can have a substantially circular or polygonal transverse cross section that extends between a first end 44 and an opposing second end 46. First end 44 terminates at a top end wall 48 while second end 46 terminates at a bottom end wall 50.

Container 32 can be comprised of one or more sheets of a flexible, water impermeable material such as a low-density polyethylene or other polymeric sheets having a thickness typically in a range between about 0.1 mm to about 5 mm with about 0.2 mm to about 2 mm being more common. Other thicknesses can also be used. The material can be comprised of a single ply material or can comprise two or more layers that are either sealed together or separated to form a double wall container. Where the layers are sealed together, the material can comprise a laminated or extruded material. The laminated material can comprise two or more separately formed layers that are subsequently secured together by an adhesive.

The extruded material can comprise a single integral sheet that comprises two or more layers of different material that are each separated by a contact layer. All of the layers are simultaneously co-extruded. One example of an extruded material that can be used in the present invention is the HyQ CX3-9 film available from HyClone Laboratories, Inc. out of Logan, Utah. The HyQ CX3-9 film is a three-layer, 9 mil cast film produced in a cGMP facility. The outer layer is a polyester elastomer coextruded with an ultra-low density polyethylene product contact layer. Another example of an extruded material that can be used in the present invention is the HyQ CX5-14 cast film also available from HyClone Laboratories, Inc. The HyQ CX5-14 cast film comprises a polyester elastomer outer layer, an ultra-low density polyethylene contact layer, and an EVOH barrier layer disposed therebetween. In still another example, a multi-web film produced from three independent webs of blown film can be used. The two inner webs are each a 4 mil monolayer polyethylene film (which is referred to by HyClone as the HyQ BM1 film) while the outer barrier web is a 5.5 mil thick 6-layer coextrusion film (which is referred to by HyClone as the HyQ BX6 film).

The material can be approved for direct contact with living cells and be capable of maintaining a solution sterile. In such an embodiment, the material can also be sterilizable such as by ionizing radiation. Examples of materials that can be used in different situations are disclosed in U.S. Pat. No. 6,083,587 that issued on Jul. 4, 2000 and U.S. Patent Publication No. US 2003/0077466 A1, published Apr. 24, 2003 that are each hereby incorporated by specific reference.

In one embodiment, container 32 comprises a two-dimensional pillow style bag wherein two sheets of material are placed in overlapping relation and the two sheets are bounded together at their peripheries to form internal chamber 40. Alternatively, a single sheet of material can be folded over and seamed around the periphery to form internal chamber 40. In another embodiment, container 32 can be formed from a continuous tubular extrusion of polymeric material that is cut to length and the ends seamed closed.

Figure 2:
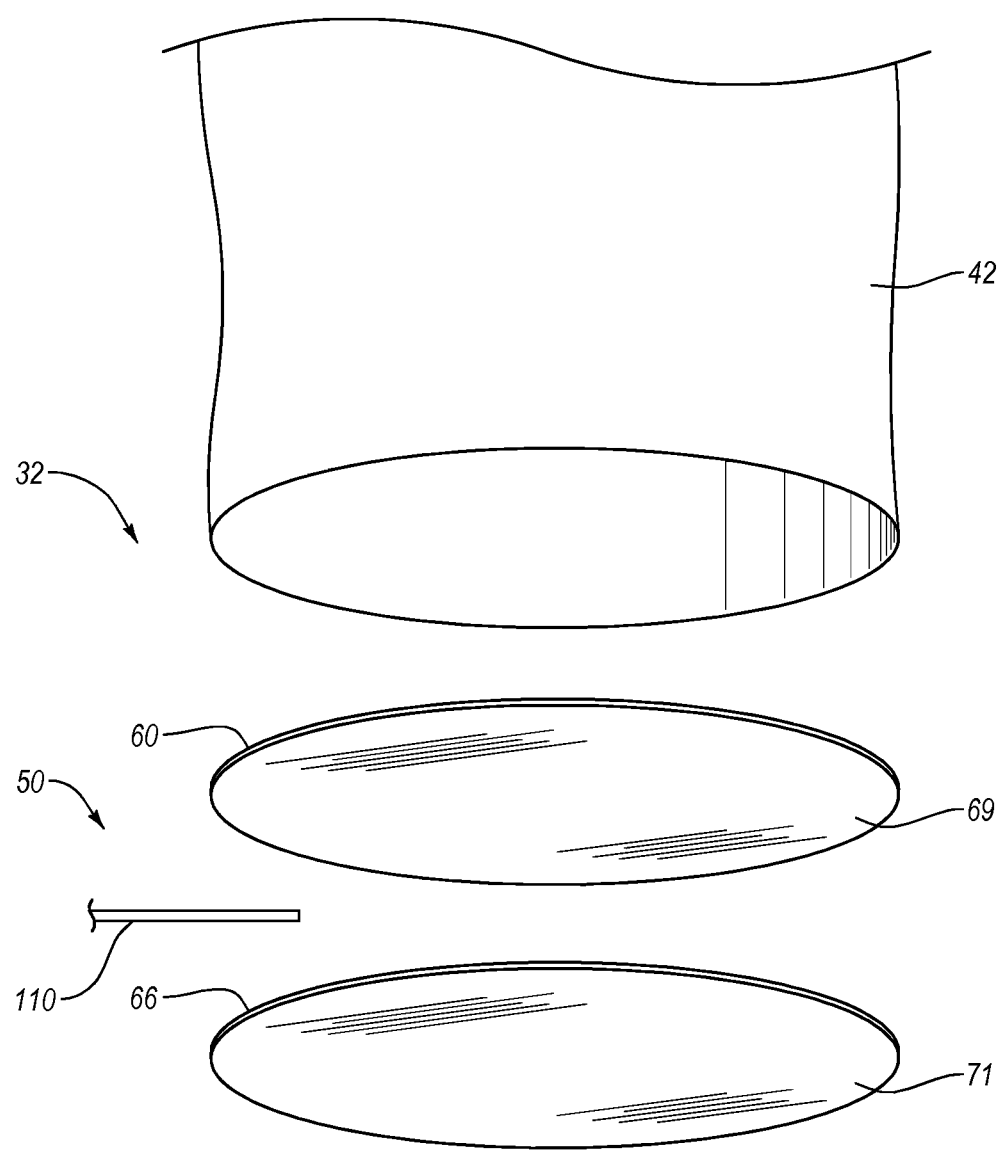
FIG. 2 is an exploded perspective view of the bottom end wall of the container assembly shown in FIG. 1.

In still other embodiments, container 32 can comprise a three-dimensional bag that not only has an annular side wall but also a two-dimensional top end wall 48 and a two-dimensional bottom end wall 50. For example, three-dimensional container 32 can comprise sidewall 42 formed from a continuous tubular extrusion of polymeric material that is cut to length, such as shown in FIG. 2. A circular top end wall 48 (FIG. 1) and bottom end wall 50 can then be welded to opposing ends of sidewall 42. In yet another embodiment, three-dimensional container 32 can be comprised of a plurality of discrete panels, typically three or more, and more commonly between four to six. Each panel can be substantially identical and comprises a portion of side wall 42, top end wall 48, and bottom end wall 50 of container 32. The perimeter edges of adjacent panels are seamed together to form container 32. The seams are typically formed using methods known in the art such as heat energies, RF energies, sonics, or other sealing energies. In alternative embodiments, the panels can be formed in a variety of different patterns.

It is appreciated that container 32 can be manufactured to have virtually any desired size, shape, and configuration. For example, container 32 can be formed having chamber 40 sized to 10 liters, 30 liters, 100 liters, 250 liters, 500 liters, 750 liters, 1,000 liters, 1,500 liters, 3,000 liters, 5,000 liters, 10,000 liters or other desired volumes. Chamber 40 can also have a volume in a range between about 10 liters to about 5,000 liters or about 30 liters to about 1,000 liters. Any other ranges selected from the above volumes can also be used. Although container 32 can be any shape, in one embodiment container 32 is specifically configured to be complementary to or substantially complementary to compartment 20 of support housing 12.

In any embodiment, however, it is typically desirable that when container 32 is received within compartment 20, container 32 is generally uniformly supported by support housing 12. Having at least generally uniform support of container 32 by support housing 12 helps to preclude failure of container 32 by hydraulic forces applied to container 32 when filled with fluid.

Although in the above discussed embodiment container 32 is in the form of a flexible bag, in alternative embodiments it is appreciated that container 32 can comprise any form of collapsible container, flexible container, or semi-rigid container. Furthermore, in contrast to having a closed top end wall 48, container 32 can comprise an open top liner. Container 32 can also be transparent or opaque and can have ultraviolet light inhibitors incorporated therein.

Mounted on top end wall 48 are a plurality of ports 52 that are in fluid communication with chamber 40. Although two ports 52 are shown, it is appreciated that one or three or more ports 52 can be present depending on the intended use of container 32. As such, each port 52 can serve a different purpose depending on the type processing to be undertaken. For example, ports 52 can be coupled with a tube 54 for dispensing fluid or undertaken. ; other components into chamber 40 or withdrawing fluid from chamber 40. In addition, such as when container 32 is used as a bioreactor for growing cells or microorganisms, ports 52 can be used to provide various probes, such as temperature probes, pH probes, dissolved oxygen probes, and the like, access to chamber 40. It is appreciated that ports 52 can come in a variety of different configurations and can be placed at any number of different locations on container 32, including sidewall 42 and bottom end wall 50.

Although not required, in one embodiment means are provided for mixing fluid 41 within chamber 40. The means for mixing can be in the form of a mixing assembly. By way of example and not by limitation, in one embodiment as shown in FIG. 1 a drive shaft 56 projects into chamber 40 and has an impeller 58 mounted on the end thereof. A dynamic seal 59 forms a seal between shaft 56 and container 32. External rotation of drive shaft 56 facilitates rotation of impeller 58 that mixes and/or suspends fluid 41 within chamber 40. Specific examples of how to incorporate a rotational mixing assembly into a flexible container are disclosed in U.S. Pat. No. 7,384,783 that issued Jun. 10, 2008 and U.S. Pat. No. 7,682,067 that issued on Mar. 23, 2010, which are incorporated herein by specific reference.

In yet another alternative embodiment of the means for mixing or the mixing assembly, mixing can be accomplished by vertically reciprocally moving a vertical mixer within chamber 40. Further disclosure with regard to the assembly and operation of vertical mixer is disclosed in U.S. Patent Publication No. 2006/0196501, published Sep. 7, 2006, which is incorporated herein by specific reference. In yet other embodiments, it is appreciated that the mixing can be accomplished by simply circulating fluid through chamber 40 such as by using a peristaltic pump to move fluid in and out of chamber 40; by rotating a magnetic impeller or stir bar within container 32 and/or by injecting sufficient gas bubbles within the fluid to mix the fluid. Other conventional mixing techniques can also be used.

Continuing with FIG. 1, bottom end wall 50 has a plurality of spargers incorporated therein. Specifically, bottom end wall 50 comprises a first sheet 60 having a first side face 62 and an opposing second side face 64. First sheet 60 overlays a second sheet 66 that likewise has a first side face 68 and an opposing second side face 70. First sheet 60 and second sheet 66 typically comprise flexible polymeric sheets such as those discussed above with regard to container 32. As discussed above with regard to bottom end wall 50, first sheet 60 can comprise a continuous sheet that is welded to side wall 42 around a perimeter edge 69 as depicted in FIG. 2. Alternatively, first sheet 60 can comprise an integral portion of sidewall 42 or can comprise a plurality of separate sheets secured together that are either attached to or are an integral portion of sidewall 42. Second sheet 66 can be welded to second side face 64 of first sheet 60 and/or welded to sidewall 42, such as along a perimeter edge 71 of second sheet 66. In other embodiments, second sheet 66 can be welded to or comprise an integral portion of sidewall 42, as discussed above with regard to first sheet 60, while first sheet 60 is welded or otherwise secured to first side face 68 of second sheet 66 and/or sidewall 42.

Figure 3:
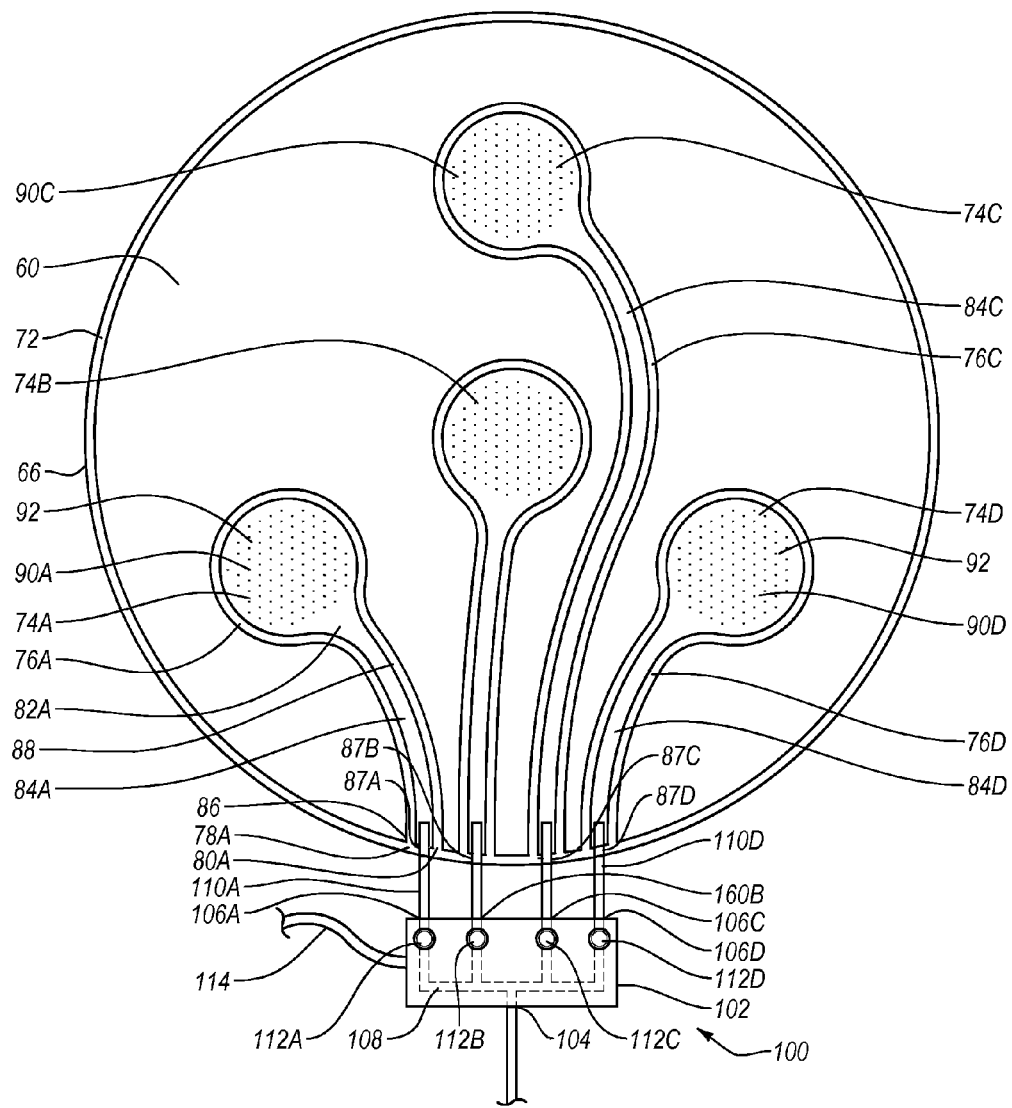
FIG. 3 is a top plan view of the bottom end wall of the container assembly shown in FIG. 1 showing the spargers formed thereon and a manifold coupled thereto.

Depicted in FIG. 3 is a top plan view of first sheet 60 overlaying second sheet 66. In this embodiment, sheets 60 and 66 are welded together by a weld line 72. Weld line 72, as with other weld lines discussed herein, can be formed using any conventional technique such as laser welding, sonic welding, heat welding, or the like. Weld line 72 is shown as welding together the perimeter or outside edges of sheets 60 and 66 but can be formed radially inward from one or both of the perimeter edges or at other locations. As also shown in FIG. 3, four separate spargers 74A-D are formed by producing other weld lines between sheets 60 and 66.

For example, sparger 74A is formed by forming a weld line 76A starts at a first location 78A located at or adjacent to the perimeter edge of sheet 60 and/or sheet 66 and extends into the interior of sheets 60 and 66 along a predetermined path for the sparger 74A and then circles back to a second location 80A at or adjacent to the perimeter edge of sheet 60 and/or sheet 66 adjacent to first location 78A. Weld line 76A bounds a perimeter of a sparger pathway 82*a* which is the area bounded between sheets 60 and 66 and partially encircled by weld line 76A. In the embodiment depicted, sparger pathway 82A comprises a gas transfer path 84A that extends from a first end 86 to an opposing second end 88. An opening 87A is formed at first end 86 between locations 78A and 80A and between sheets 60 and 66 through which a gas can be fed into gas transfer path 84A. Sparger pathway 82A also comprises a sparging area 90A formed at second end 88 that is in fluid communication with gas transfer path 84A. In the embodiment depicted, gas transfer path 84A is a narrow elongated path while sparging area 90A forms an enlarged circular area. Other configurations can also be used.

A plurality of perforations 92 extend through first sheet 60 of sparging area 90A so that gas can pass along gas transfer path 84A, into sparging area 90A and then out through perforation 92 to form gas bubbles within fluid 41 disposed within chamber 40. Spargers 74B-D are similarly formed with like reference characters being used to identify like elements. By using this technique, a plurality of discrete spargers can be easily formed on container 32. Each sparger can be disposed at any desired location and be any desired size, shape or configuration. Likewise, although four spargers 82 are shown, it is appreciated that any number of spargers such as 1, 2, 3, 5, or more can be formed with sheets 60 and 66. The sparging areas can be uniformly distributed over sheets 60 and 66 or can be located at defined locations for optimal sparging. For example, a sparger can be disposed directly below the means for mixing such that the mixing or movement of fluid 41 produced by the mixer helps to entrain the gas bubbles within fluid 41.

In some embodiments, each sparger can have the same number of perforations 92 and all perforations 92 can be the same size and shape. In alternative embodiments, perforations 92 can be different between two or more different spargers. For example, different spargers can have different numbers, sizes, and/or shapes of perforations 92 to optimize performance in different situations. Larger perforations 92 produce larger gas bubbles that may be optimal for stripping $CO_2$ from fluid 41 whereas smaller perforations produce smaller bubbles that may be preferred for oxygenating fluid 41. Likewise, increasing the number of perforations 92 may be helpful in causing the bubbles to mix the fluid and/or increase stripping or oxygenation. In other embodiments, it is appreciated that one or more of spargers 74A-D can have combinations of different perforations 92. For example, a single sparger can have both small and large perforations 92. In one embodiment, the smaller bubbles are formed from perforations 92 typically having a diameter of less than 0.8 mm, 0.4 mm or 0.2 mm, 0.1 mm while the large bubbles are formed from perforation typically having a diameter greater than 1.5 mm, 0.8 mm, 0.4 mm or 0.15 mm. Perforations of other diameters can also be used. The size of the perforation and resulting bubbles depends on the intended use and the size of container 32. For example, the large bubbles are typically larger when processing a large volume of fluid in a large container than when processing a relatively small volume of fluid in a small container. The variance or delta between the diameter of the perforations for the small bubbles and the perforations for the large bubbles is typically at least 0.15 mm, 0.3 mm, 0.5 mm or 1 mm and is often within ±0.1 mm or ±0.5 of these values. Other variances can also be used.

As discussed below in greater detail, spargers 74A-D can simultaneously operate or, alternatively, a manifold or other regulator can be used so that one or more of the spargers can be operated while the other spargers are not operated. Accordingly, by having different spargers with different perforations 92, select spargers can be used in different situations or times to optimize performance.

In some embodiments, it is appreciated that gas transfer path 84A of sparger 74A is not required. For example, perforations 92 can be formed through first sheet 60 overlying gas transfer path 84A so as to convert gas transfer path 84A in a portion of sparging area 90A. It is appreciated that perforations 92 can be formed using any conventional techniques. For example, perforations 92 can be formed as part of the manufacturing process for the sheet or can be subsequently produced by punches or other techniques. In one embodiment, one or more lasers can be used to form perforations 92. An advantage of using a laser is that perforations 92 can be formed at precise locations and with a precise diameter so that bubbles can be formed having a precise, predefined size. Furthermore, when a laser is used to form a perforation, the material melted by the laser gathers around the perimeter edge of the perforation, thereby reinforcing the perforation and helping to prevent rupture of the sheet.

In one embodiment of the present invention, a manifold can be used for controlling the gas flow to one or more of spargers 74A-D. For example, depicted in FIG. 3 is one embodiment of a manifold 100 incorporating features of the present invention. Manifold 100 comprises a body 102 having a gas inlet port 104 and a plurality of gas outlet ports 106A-D. Gas outlet ports 106A-D are in parallel communication with gas inlet port 104 by way of a forked flow path 108. A gas source, such as a compressor or a canister of compressed gas, is fluid coupled with gas inlet port 104. The gas can be air, oxygen, or any other gas or combination of gases. Gas lines 110A-D extend from gas outlet ports 106A-D, respectively, to a corresponding opening 87A-D at first end 86 of each sparger 74A-D, respectively. Gas lines 110A-D can be welded between sheets 60 and 66 at openings 87A-D so as to seal openings 87A-D closed. Gas lines 110A-D can comprise flexible or rigid tubes and can be integrally formed with or separately attached to body 102.

Valves 112A-D are mounted on body 102 and control the flow of gas to each gas line 110A-D, respectively. In one embodiment, valves 112A-D can be electrical valves, such as solenoid valves, that can be used to open, close, or restrict the flow of gas to spargers 74A-D. In this embodiment, electrical wiring 114 can couple to valves 112A-D for controlling their operation. In other embodiments, valves 112A-D can comprise valves that are operated manually, hydraulically, pneumatically, or otherwise. By using manifold 100, different spargers or different combinations of spargers can be used at different times to optimize performance as discussed above.

Figure 4:
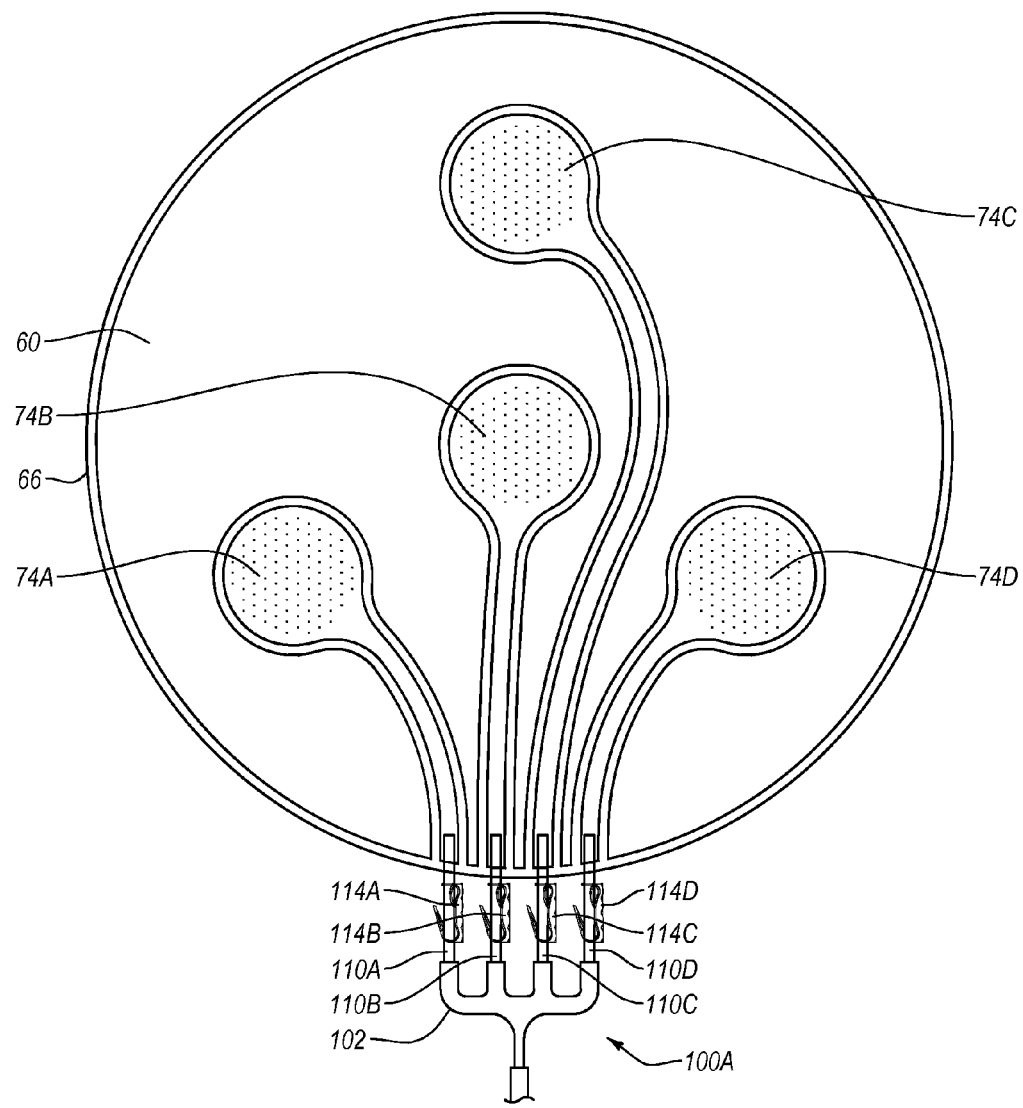
FIG. 4 is a top plan view of the container assembly shown in FIG. 3 having an alternative manifold coupled thereto.

Depicted in FIG. 4 is an alternative embodiment of a manifold 100A wherein like elements between manifold 100 and 100A are identified by like reference characters. Manifold 100A includes body 102 having gas lines 110A-D projecting therefrom and communicating with spargers 74A-D. In manifold 100A, gas lines 110A-D comprise flexible tubing. In turn, manifold 100A has valves 114A-D in the form of pinch clamps or hose clamps that are mounted on gas lines 110A-D, respectively. It is appreciated that pinch clamps 114 can come in a variety of different configurations and are used to manually pinch gas lines 110A-D so as to control the flow of gas therethrough.

Figure 5:
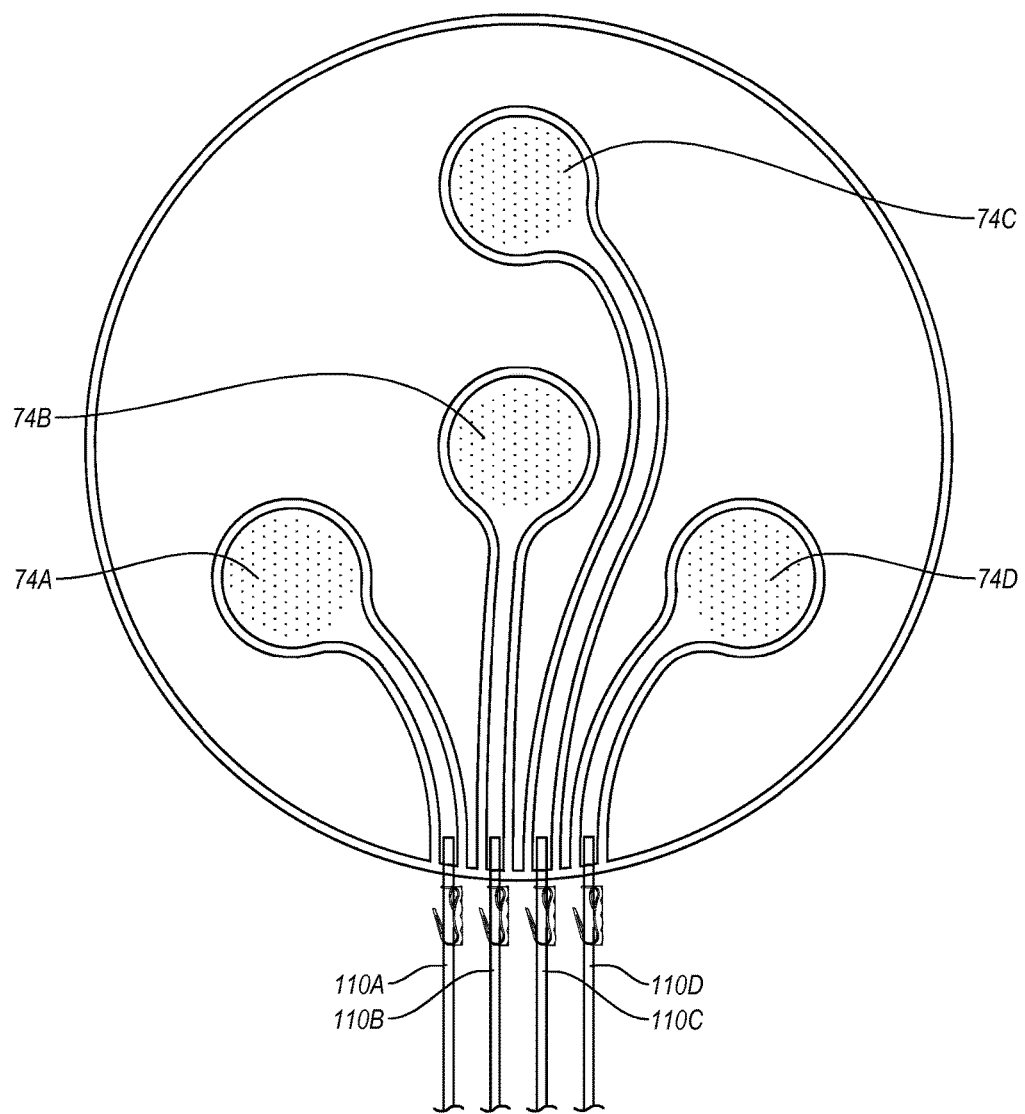
FIG. 5 is a top plan view of the bottom end wall shown in FIG. 3 having a plurality of discrete gas lines coupled thereto.

In other alternative embodiments, it is appreciated that a manifold is not required. For example, as depicted in FIG. 5, gas lines 110A-D can extend from spargers 74A-D and have valves 114A-D coupled thereon, respectively. However, gas lines 110A-D need not be part of or coupled with a manifold but rather can be separately coupled to discrete gas sources if desired.

Figure 6:
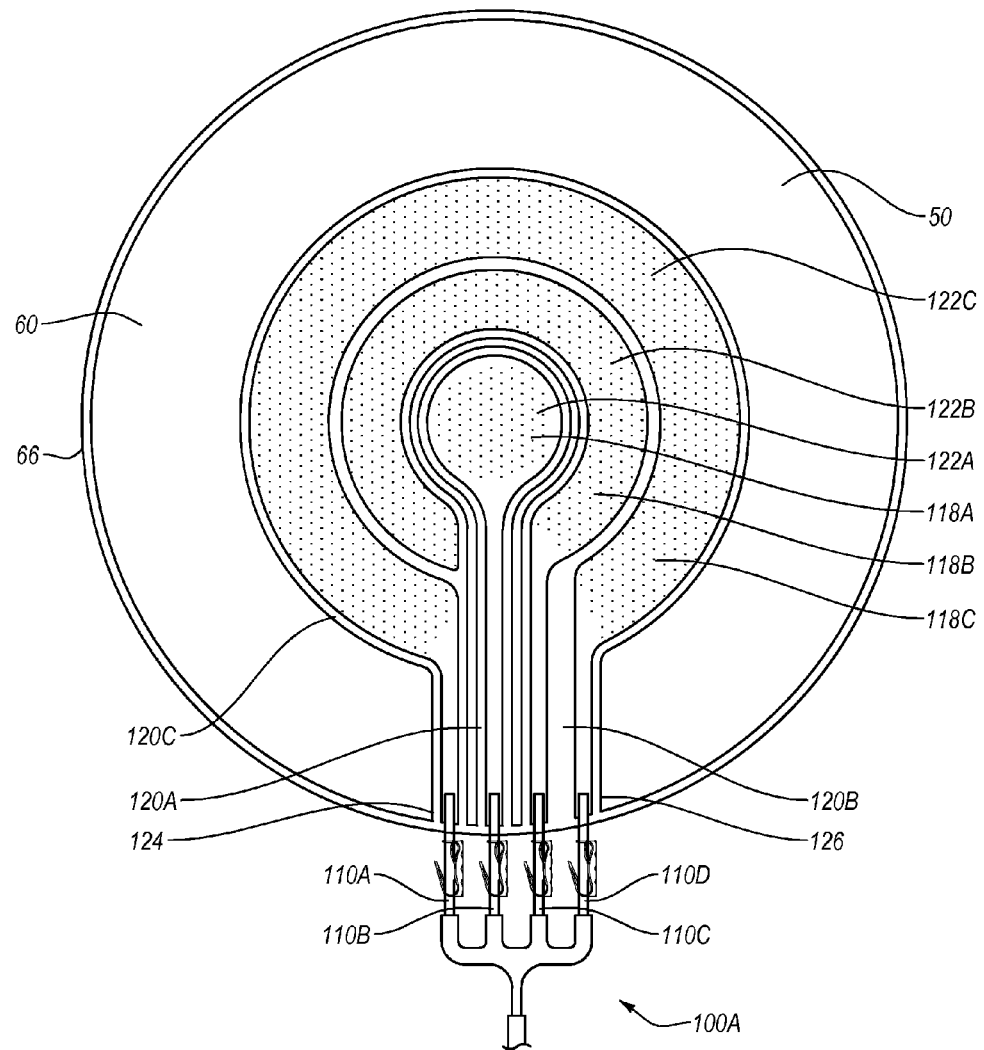
FIG. 6 is a top plan view of a bottom end wall of a container assembly having an alternative configuration of spargers formed thereon.

As previously discussed, any desired number, size, shape, and/or configuration of spargers can be formed. For example, depicted in FIG. 6 is a top plan view of bottom end wall 50 having three spargers 118A-C formed thereon. Again, the perimeter of each sparger 118A-C is formed by weld lines 120A-C, respectively, formed between sheets 60 and 66. If desired, a single weld line can form a common boundary between adjacent spargers. For example, weld line 120B is shown forming a common boundary between spargers 118B and 118C. Sparger 120A is similar to sparger 74A expect that sparger 118A is more centrally located on sheets 60 and 66. Sparger 118B has a substantially C-shaped sparging area 122B that curves around sparging area 122A. Likewise, sparger 118C has a sparging area 122C that substantially encircles around sparging area 122B.

In contrast to the prior spargers, sparger 118C has a first end 124 and an opposing second end 126 with gas lines 110A and 110D fluid coupled therewith, respectively. In this configuration, a gas can be supplied through both gas lines 110A and 110D at opposing ends of sparger 118C so that the gas is more uniformly provided to sparging area 122C. As a result, the gas exits out of all of perforations 92 at a more uniform pressure and flow rate. Again, the flow of gas into each of spargers 118A-C can be controlled by the depicted manifold 100A or any other type of manifold.

In the embodiment depicted in FIG. 6, impeller 58 (FIG. 1) can be vertically aligned with sparger 118A while sparger 118C is laterally spaced apart from impeller 58. Sparger 118A can be designed to produce small bubbles that interact with and are distributed by impeller 58 throughout the fluid. By dispersing the small bubbles by using impeller 58, the small bubbles have a longer dwell time within the fluid which enhances mass transfer of the gas. For example, the bubbles can more efficiently oxygenate the fluid. Sparger 118C produces larger bubbles that do not directly interact with impeller 58. The larger bubbles are commonly used for stripping $CO_2$ from the fluid. Because the larger bubbles have a higher buoyancy than the smaller bubbles, the impeller has less of an influence on the larger bubbles and thus there may be no need for aligning them with the impeller. Furthermore, the impeller may break up the larger bubbles making them less efficient for stripping $CO_2$. In addition, aligning the larger bubbles with the impeller can cause the impeller to cavitate which reduces mixing efficiency of the fluid. In other embodiments, however, sparger 118A can be designed to produce large bubbles that are intentionally broken up and dispersed by impeller 58 while sparger 118C produces small bubbles that do not directly interact with impeller 58. Other configuration can also be used.

Figure 7:
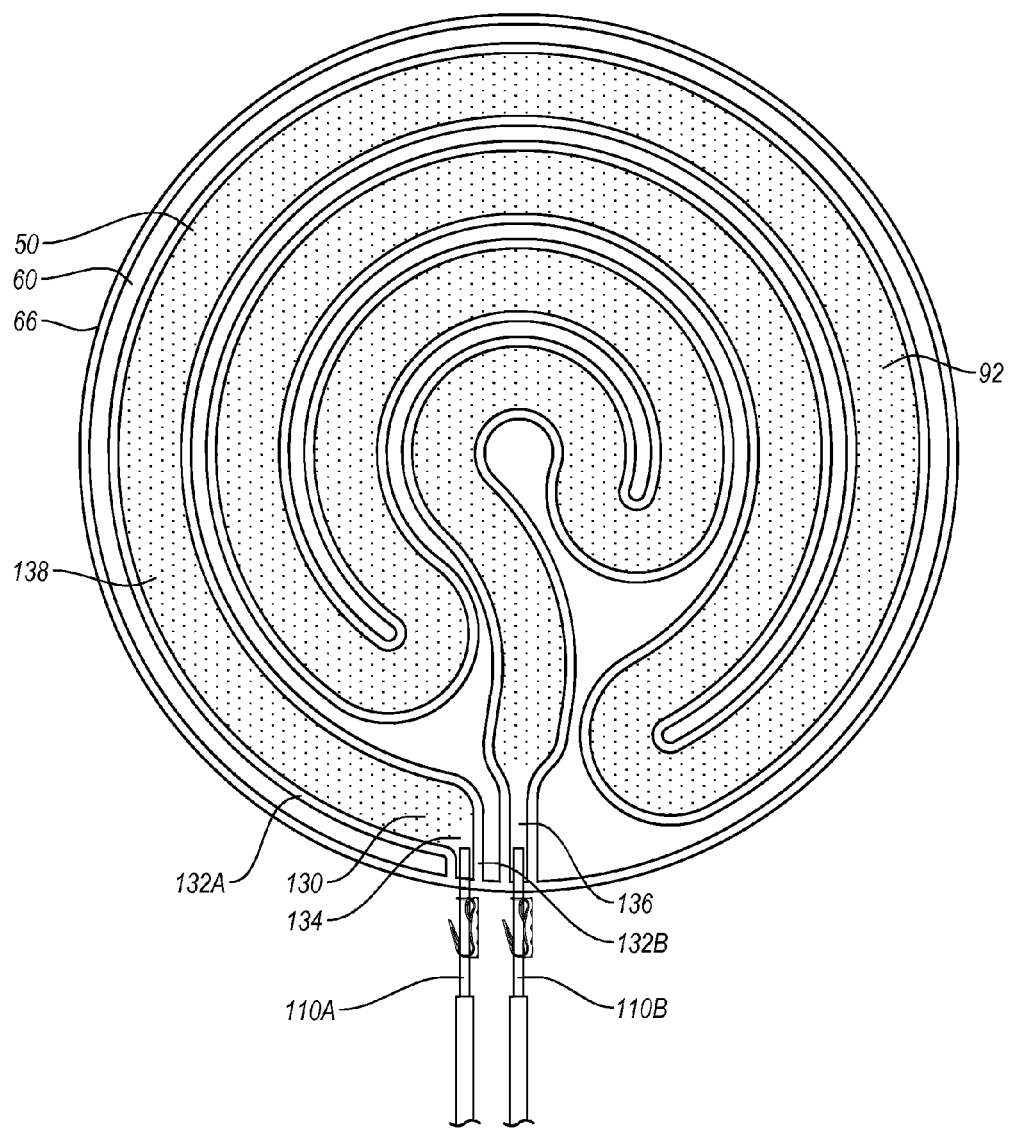
FIG. 7 is a top plan view of a bottom end wall of a container having an alternative embodiment of a sparger mounted thereon.

In another embodiment, it may be desirable to have a single sparger that covers a large portion of bottom end wall 50 so that the fluid within the container can be more uniformally sparged. For example, depicted in FIG. 7 is a sparger 130 having a first end 134 and an opposing second end 136 with a perimeter bounded by weld lines 132A and 132B extending therebetween. Sparger 130 is elongated and snakes along bottom end wall 50 in a curving pattern. Sparger 130 has a sparging area 130, i.e., the area between weld lines 132A and 132B, that covers at least 40% and more commonly at least 50%, 60% or 80% of the surface area of one side of bottom end wall 50. Other percentages can also be used. Gas lines 110A and 110B are coupled with the opposing ends of sparger 130 so that a gas can be delivered to the opposing ends of sparger 130. As a result, the gas is more uniformly passed out through perforations 92 than if only a single gas line was used.

Figure 8:
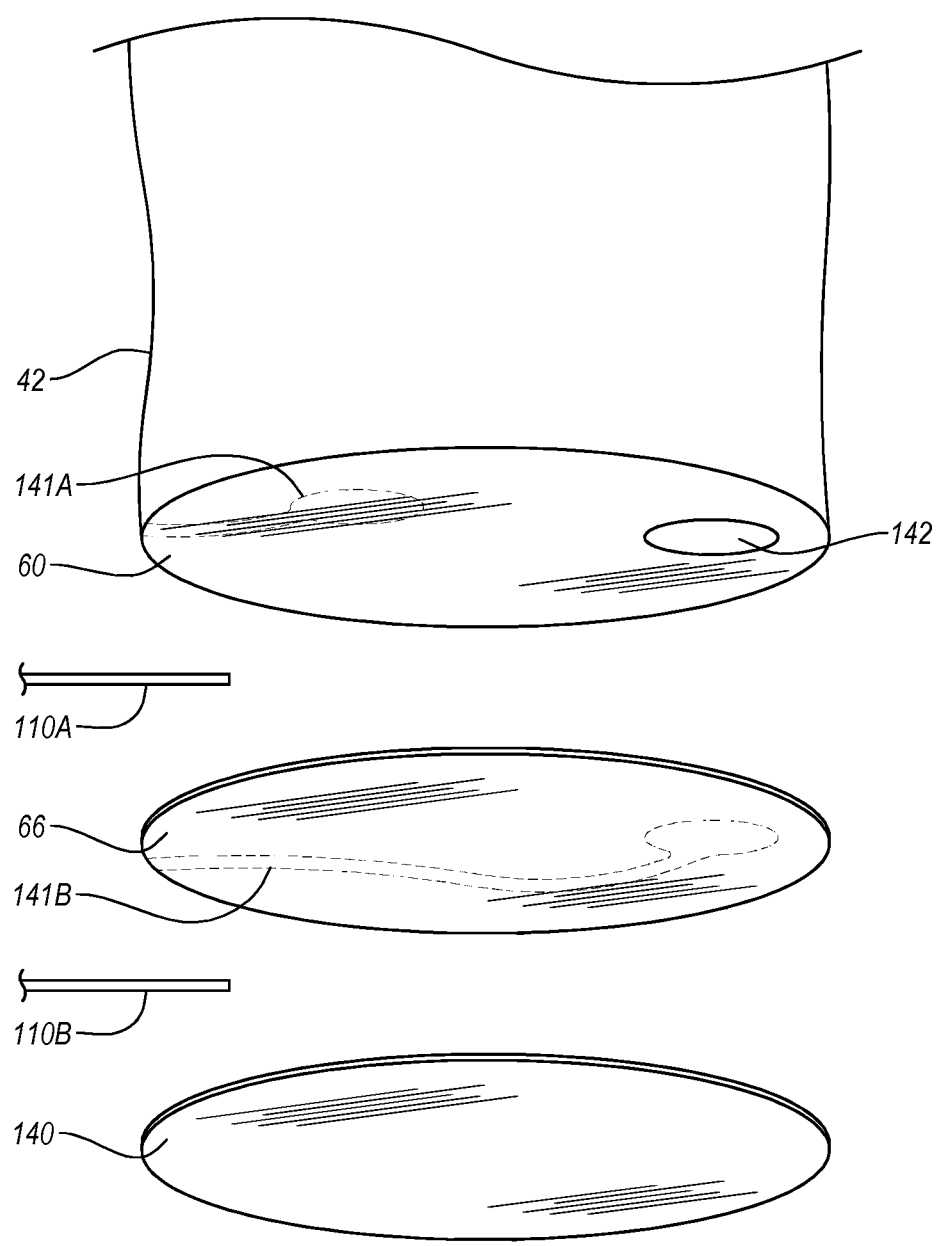
FIG. 8 is an exploded perspective view of a bottom end wall of a container containing three sheets.

Turning to FIG. 8, in one alternative embodiment the inventive spargers can be formed by overlaying three or more sheets. For example, one or more weld lines can weld sheet 60 to sheet 66 so as to form a sparger, represented by broken lines 141A, therebetween. Likewise, one or more weld lines can weld sheets 66 and 140 together so as to form a sparger, represented by broken lines 141B, therebetween. An opening 142 can be formed through sheet 60 so as to expose the sparging area of sparger 141 B formed between sheets 66 and 140. It is also appreciated that the weld lines can simultaneously weld all three sheets 16, 60, and 140 together to form sparger 141A and/ or 141B. Gas lines 110A and B couple to and deliver gas to spargers 141A and 141B, respectively.

Figure 9:
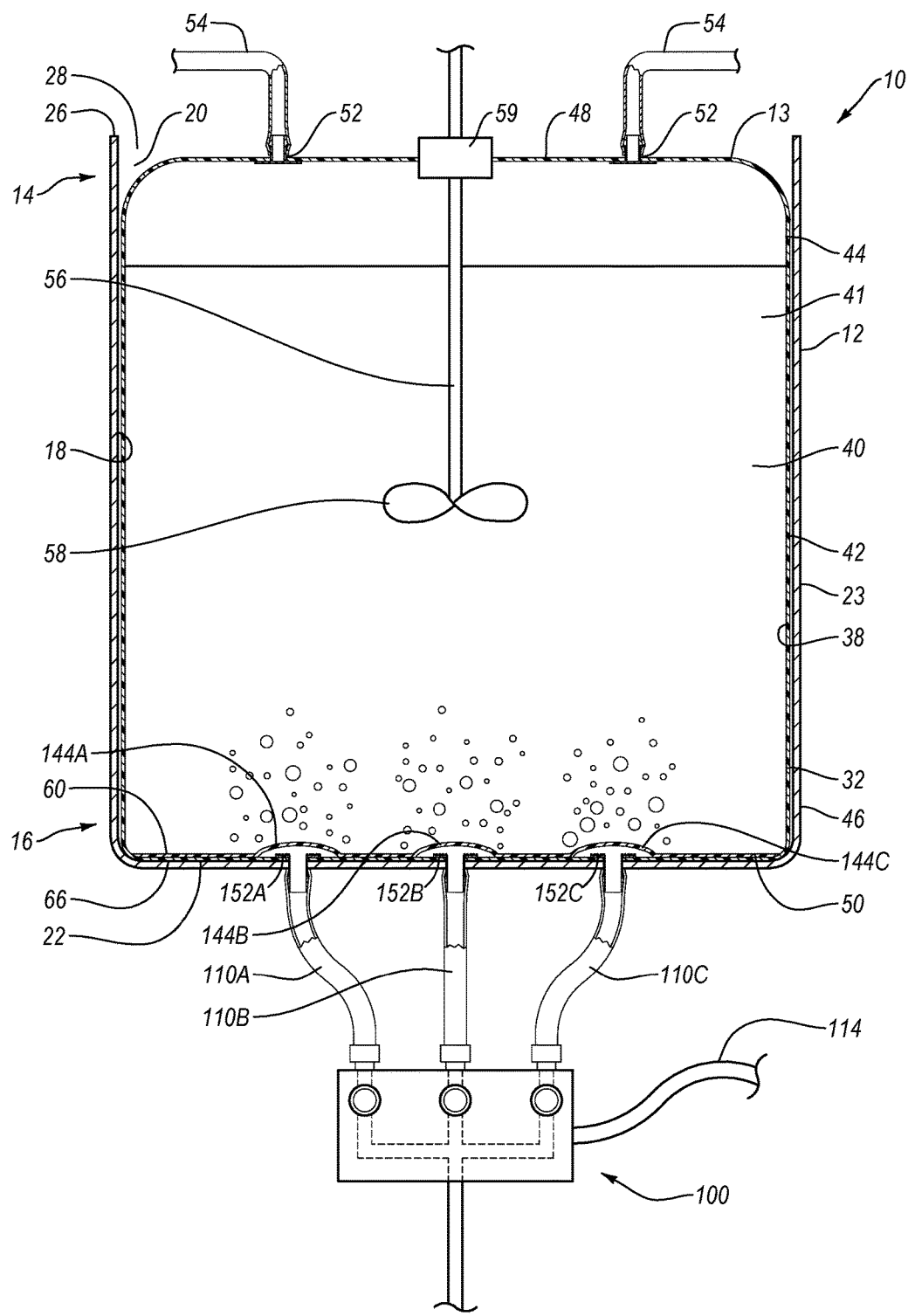
FIG. 9 is a cross sectional side view of an alternative embodiment of a container assembly having spargers extending down through the bottom end wall.
Figure 10:
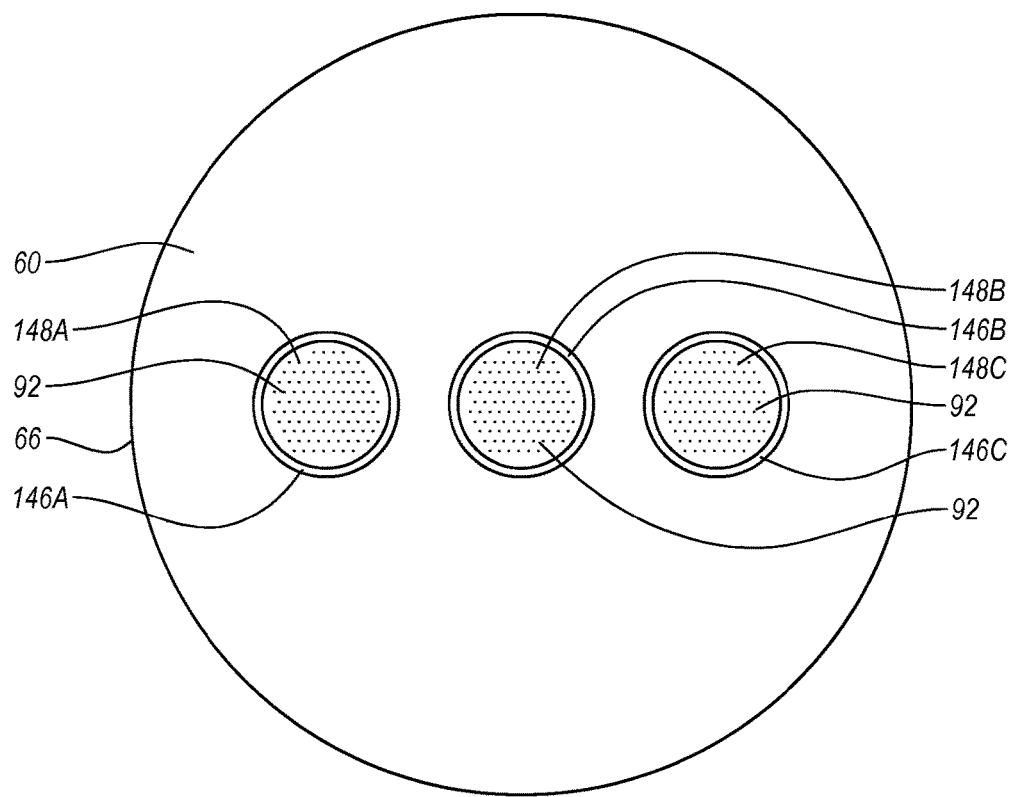
FIG. 10 is a top plan view of the bottom end wall of the container shown in FIG. 9.

In the previous embodiments, the gas lines feeding gas to the spargers entered through an opening, such as openings 87A-D in FIG. 3, formed between sheets 60 and 66. This configuration enables the gas lines to project radially out from the side of container 32 and thus to project through an opening 24 (FIG. 1) in side of support housing 12. In an alternative embodiment, however, the gas lines can fluid couple with the spargers so as to project down from the bottom of bottom end wall 50 and in turn project down through floor 22 of support housing 12. For example, as depicted in FIG. 9, bottom end wall 50 of container 32 is again comprised of first sheet 60 overlapping second sheet 66 which are welded together to form spargers 144A-C. Specifically, in the top plan view as shown in FIG. 10, weld lines 146A-C weld sheets 60 and 66 together and are each formed in a circular pattern so as to bound a perimeter of sparging areas 148A-C, respectively. In alternative embodiment, it is appreciated that weld lines 146A-C can be formed in any encircling pattern. Spargers 144A-C also include perforations 92 formed through first sheet 60 overlaying each sparging area 148.

Figure 11:
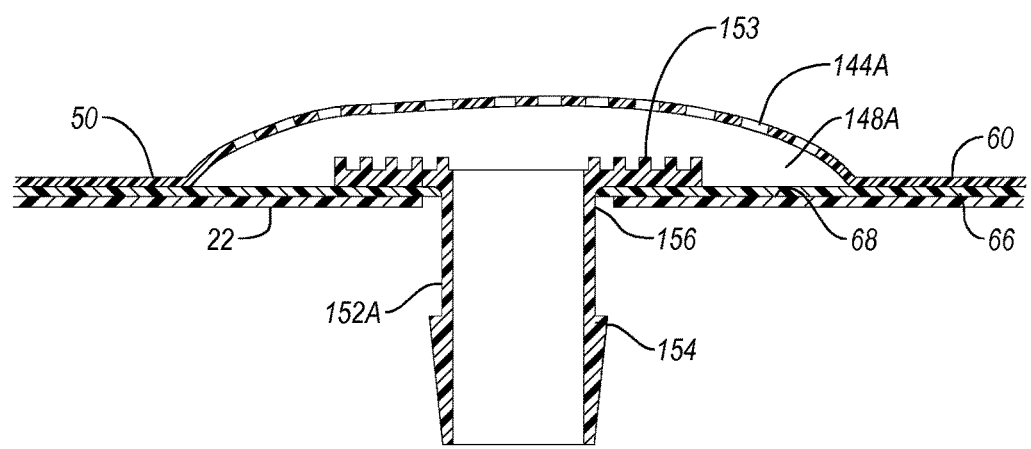
FIG. 11 is a cross sectional side view of one of the spargers shown in FIG. 9.
Figure 12:
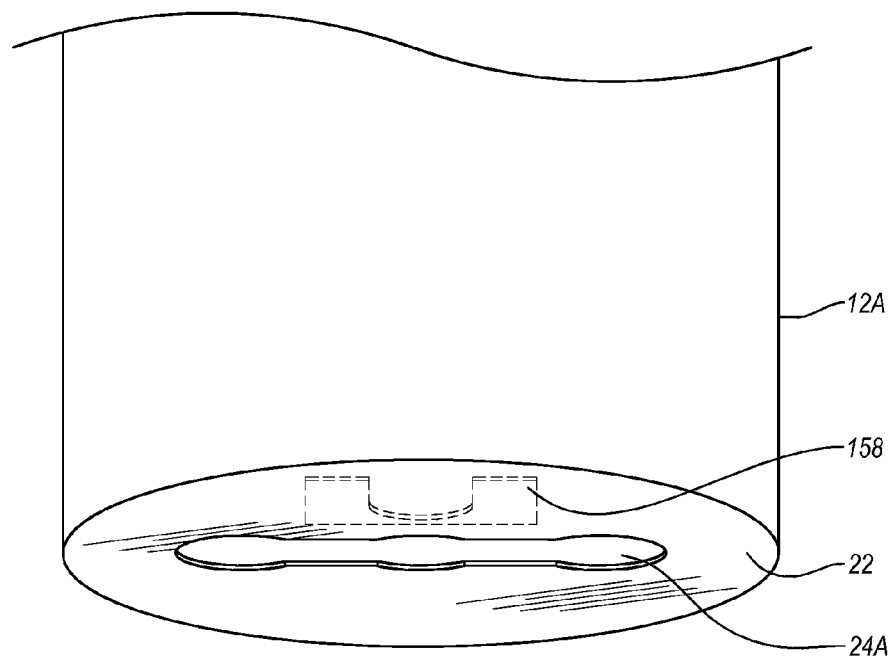
FIG. 12 is a perspective view of the floor of the support housing shown in FIG. 9.

As depicted in FIGS. 9 and 11, a port 152A has a flange 153 that is mounted on first side face 68 of second sheet 66 so that a stem 154 extends down through an opening 156 in sheet 66. As a result, port 152A communicates with sparging area 148A of sparger 144A. Ports 152B and C are similarly coupled with spargers 144B and C. As shown in FIG. 9, a first end of gas lines 110A-C is coupled with ports 152A-C, respectively, while an opposing second end of gas lines 110A-C is coupled with manifold 100. As a result, manifold 100 can be used to control selective operation of each of the spargers 144A-C. Again, spargers 144A-C can be of any desired size, shape or configuration.

Depending on the desired configuration for the containers and spargers, it is appreciated that the containers can be assembled using a variety of different procedures. For example, either before or after cutting sheets 60 and 66 to their desired size, perforations 92 can be formed on first sheet 60 having the desired number, size, shape and location. Likewise, where applicable, openings 156 can be formed on second sheet 66 and ports 152 welded thereto. Next, sheets 60 and 66 can be overlapped and the various weld lines formed so as to weld sheets 60 and 66 together and produce the spargers. Where ports 156 are not used, gas lines can be welded within the opening formed between sheets 60 and 66 so as to communicate with the spargers. Finally, sheets 60 and 66 can be welded to side wall 42. Alternatively, sheet 60 can be welded to side wall 42 and then second sheet 66 can be welded to first sheet 60 for welding the sheets together and forming the spargers. In yet other embodiments, first sheet 60 can be integrally formed with side wall 42 or side wall 42 and first sheet 60 can comprise multiple sections that are welded together. In these configurations, second sheet 66 would subsequently be welded to the combination of first sheet 60 and side wall 42. In other embodiments, second sheet 66 can be attached to or be integrally formed with side wall 42 while first sheet 60 can comprise a smaller sheet or multiple smaller sheets that only cover a portion second sheet 66. Once the gas lines are coupled with different spargers and, where appropriate, a manifold coupled thereto, all gas lines and ports coupled to the container are closed off and the full assembly is sterilized by radiation or other traditional techniques.

To facilitate use, the container assembly 13 is lowered into compartment 20 of support housing 12. The related manifold and/or gas lines are then passed out of compartment 20 through opening 24, when support housing 12 shown in FIG. 1 is used. In the embodiment shown in FIG. 9, the manifold and gas lines can pass down through an elongated opening 24A formed in floor 22 of support housing 12A. In both embodiments, a plate 158 can be used to help cover a portion of opening 24 or 24A after the manifold is passed therethrough so as to minimize the size of the openings. This covering of the openings reduced stress on the container caused by fluid trying to push the container through the openings. Container assembly 13 can be partially inflated with a gas after it is positioned within support housing 12 to enable it to be manually adjusted and properly positioned within support housing 12. Alternatively, container assembly 13 can be filled with fluid while it is adjusted for proper positioning. Container assembly 13 can subsequently be used as a bioreactor, fermentor, or for simply processing fluids or chemicals.

Figure 13:
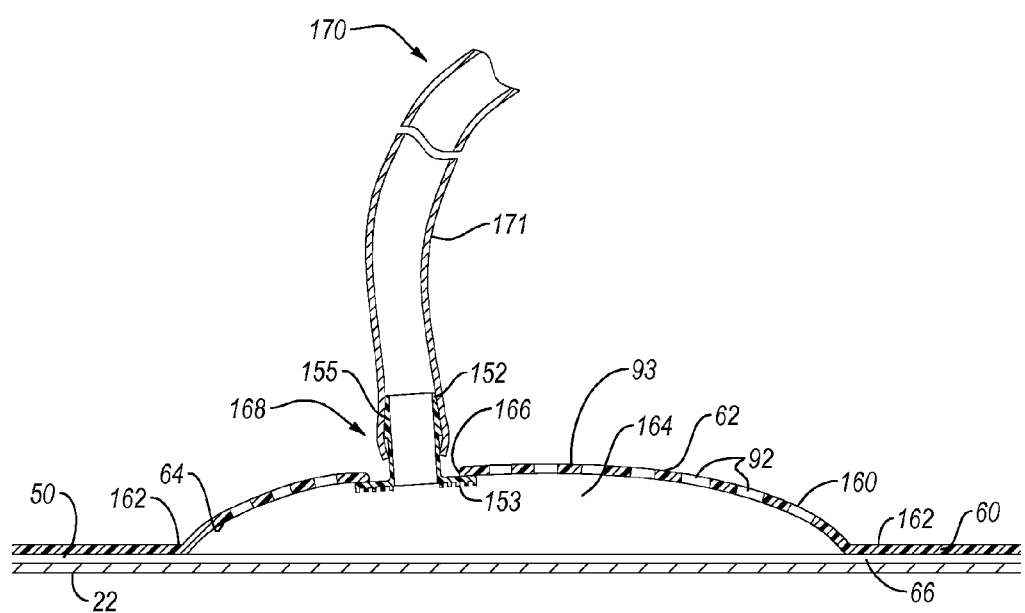
FIG. 13 is a cross sectional side view of an alternative embodiment of a sparger where a gas line projects from the sparger up into the container.

In another alternative embodiment of the present invention, the gas lines can fluid couple with the spargers so as to project up from the top of bottom end wall 50 and in turn couple with or extend out through a port 52 (FIG. 1) located at the upper end of container 32. For example, as depicted in FIG. 13, bottom end wall 50 of container 32 is again comprised of first sheet 60 overlapping second sheet 66 which are welded together to form a sparger 160. Specifically, in the same manner as previously discussed with regard to FIG. 10, a weld line 162 can weld sheets 60 and 66 together in a circular pattern so as to bound a perimeter of a sparging area 164. In alternative embodiments, it is appreciated that weld line 162 can be formed in any encircling pattern and that any number of separate spargers 160 can be formed. It is again appreciated that first sheet 60 need only be large enough to form sparger 160 or multiple spargers 160 and need not be as large as second sheet 66. Sparger 160 also includes perforations 92 formed through first sheet 60 overlaying sparging area 164.

Flange 153 of port 152 is mounted on second side face 64 of first sheet 60, such as by welding or adhesive, so that stem 154 extends out through an opening in sheet 66. As a result, port 152 communicates with sparging area 164. A first end 168 of a gas line 171 is coupled with a barbed end 155 of port 152 while an opposing second end 170 of gas line 171 is either coupled with or extends out through one of ports 52 (FIG. 1) of container 32. It is appreciated that port 52 to which gas line 171 couples or extends out can be located at the upper end of container 32, as shown in FIG. 1, or can be located at any location along sidewall 42 or on floor 50. One method for coupling second end 170 of gas line 171 to port 52 is disclosed in U.S. Pat. No. 7,225,824, issued Jun. 5, 2007 which is incorporated herein by specific reference. In turn, second end 170 of gas line 171 can be placed in communication with a gas source for delivering gas to sparger 160. Gas line 171 can also be coupled with a manifold which can control the flow of gas to multiple separate spargers 160 formed on bottom end wall 50.

It is appreciated that the inventive spargers and related containers have a variety of unique advantages over conventional spargers. For example, the inventive spargers can be easily formed by simply welding two sheets together. This welding can be achieved using the same equipment and techniques used in forming the container. This ease in manufacturing permits greater versatility in forming spargers of desired size, orientation, configuration, location, number and the like to optimize desired processing parameters. Furthermore, the spargers are flexible and are part of the bag or container. This enables the combined container and spargers to be easily rolled up or folded without potential risk of damage to the assembly. The rolled or folded assembly can be easily sterilized, stored, shipped, and incorporated into a rigid support housing. The ability to produce multiple spargers at the bottom of the bag also enables spargers to be formed with different perforations sizes so that different bubble sizes and numbers can be selectively produced to achieve different objectives. Furthermore, by using the manifolds, operation of the different spargers or sparger combinations can be controlled to further optimize processing parameters. Because the combined container and spargers are relatively inexpensive to make, the assembly can be designed as a disposable, single use item, thereby eliminating cleaning and sterilization between uses. The spargers are also flush with the floor so that they do not obstruct the flow of fluid or the flow of cells or microorganisms within the fluid.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A container assembly comprising:
   a flexible bag having an interior surface bounding a chamber and an opposing exterior surface, the bag having a top end wall, a bottom end wall, and an encircling sidewall extending therebetween, the bottom end wall being comprised of a first polymeric sheet overlying a second polymeric sheet, the first and second polymeric sheets each being comprised of a flexible film, the first polymeric sheet having an interior surface that forms a portion of the interior surface of the flexible bag that bounds the chamber and the second polymeric sheet having an exterior surface that forms a portion of the exterior surface of the flexible bag;
   a first weld line welding the first polymeric sheet to the second polymeric sheet, the first weld line forming a perimeter of a first sparger pathway formed between the first polymeric sheet and the second polymeric sheet, the first sparger pathway comprising a first gas transfer path and a first sparging area that are both bounded between the first polymeric sheet and the second polymeric sheet and both have a perimeter formed by the first weld line, the first gas transfer path being constricted relative to the first sparging area and extending from a first end to an opposing second end, and the first sparging area being formed at the second end of the first gas transfer path and communicating with the first gas transfer path; and
   a plurality of first perforations being formed through a portion of the first polymeric sheet that overlies the first sparging area so that gas can pass from the first sparging area, through the first perforations and into the chamber of the bag,
   wherein the flexible bag including the sheets of the bottom end wall thereof are sufficiently flexible so that the flexible bag including the sheets of the bottom end wall thereof can be rolled up without damage.

2. The container assembly as recited in claim 1, wherein the first gas transfer path is elongated while the first sparging area is substantially circular.

3. The container assembly as recited in claim 1, wherein there are no perforations extending through the portion of the first polymeric sheet that overlie the first gas transfer path.

4. The container assembly as recited in claim 1, further comprising a first gas line coupled with the first end of the first gas transfer path.

5. The container assembly as recited in claim 1, further comprising a first gas line welded between the first polymeric sheet and the second polymeric sheet.

6. The container assembly as recited in claim 1, further comprising a hole formed on the second polymeric sheet, a port secured to the second polymeric sheet and extending through the hole, and a first gas line coupled with the port.

7. The container assembly as recited in claim 1, further comprising a hole formed on the first polymeric sheet, a port secured to the first polymeric sheet and extending through the hole, and a first gas line coupled with the port.

8. The container assembly as recited in claim 1, further comprising:
a second weld line welding the first polymeric sheet to the second polymeric sheet, the second weld line bounding a second sparging area formed between the first polymeric sheet and the second polymeric sheet; and
a plurality of second perforations being formed through a portion of the first polymeric sheet that overlies the second sparging area.

9. The container assembly as recited in claim 8, wherein the first perforations have a different size or number than the second perforations.

10. The container assembly as recited in claim 8, further comprising a manifold in fluid communication with the first sparging area and the second sparging area.

11. The container assembly as recited in claim 10, wherein the manifold comprises:
a body with a gas inlet port and a plurality of gas outlet ports, the gas inlet port being in fluid communication with each of the plurality of gas outlet ports;
a first gas line being in fluid communication with the first sparging area and a first one of the gas outlet ports; and
a second gas line being in fluid communication with the second sparging area and a second one of the gas outlet ports.

12. The container assembly as recited in claim 10, wherein the manifold comprises:
a first valve that regulates the flow of gas through the manifold and to the first sparging area; and
a second valve that regulates the flow of gas through the manifold and to the second sparging area.

13. The container assembly as recited in claim 12, wherein the first valve and the second valve are electrically operated.

14. The container assembly as recited in claim 12, wherein the first valve and the second valve each comprise a hose clamp.

15. The container assembly as recited in claim 1, further comprising a rigid support housing bounding a compartment, the flexible bag being disposed within the compartment of the support housing.

16. The container assembly as recited in claim 1, further comprising the bag having a top end wall, the bottom end wall, and an encircling sidewall extending therebetween, the first polymeric sheet or the second polymeric sheet being connected directly to or being integrally formed as a single continuous member with at least a portion of the encircling sidewall.

17. The container assembly as recited in claim 1, wherein the first weld line traverses a path within an interior area of the first and second polymeric sheets, away from a perimeter of the first polymeric sheet and the second polymeric sheet.

18. The container assembly as recited in claim 1, wherein both the first polymeric sheet and the second polymeric sheet extend to the encircling side wall.

19. The container assembly as recited in claim 1, further comprising:
a second weld line welding the first polymeric sheet to the second polymeric sheet, the second weld line forming a perimeter of a second sparger pathway formed between the first polymeric sheet and the second polymeric sheet, the second sparger pathway comprising a second gas transfer path and a second sparging area that are both bounded between the first polymeric sheet and the second polymeric sheet, the second gas transfer path being constricted relative to the second sparging area and extending from a first end to an opposing second end, and the second sparging area being formed at the second end of the second gas transfer path and communicating with the second gas transfer path; and
a plurality of second perforations being formed through a portion of the first polymeric sheet that overlies the second sparging area so that gas can pass from the second sparging area, through the second perforations and into the chamber of the bag.

20. The container assembly as recited in claim 19, wherein the first sparger pathway is isolated from the second sparger pathway so that a gas entering the first sparger pathway does not enter the second sparger pathway.

21. The container assembly as recited in claim 1, further comprising:
the first polymeric sheet having an exterior surface that communicates with the first sparger pathway; and
the second polymeric sheet having an interior surface that communicates with the first sparger pathway.

22. A container assembly comprising:
a flexible bag having an interior surface bounding a chamber and an opposing exterior surface, the bag having a bottom end wall being comprised of a first polymeric sheet overlying a second polymeric sheet;
a first weld line welding the first polymeric sheet to the second polymeric sheet, the first weld line bounding a first sparging area formed between the first polymeric sheet and the second polymeric sheet, a plurality of first perforations being formed through a portion of the first polymeric sheet that overlies the first sparging area; and
a second weld line welding the first polymeric sheet to the second polymeric sheet, the second weld line bounding a second sparging area formed between the first polymeric sheet and the second polymeric sheet, a plurality of second perforations being formed through a portion of the first polymeric sheet that overlies the second sparging area, the first sparging area being separated from the second sparging area.

23. The container assembly as recited in claim 22, further comprising a manifold in fluid communication with the first sparging area and the second sparging area.

24. The container assembly as recited in claim 23, wherein the manifold comprises:
a first valve that regulates the flow of gas through the manifold and to the first sparging area; and
a second valve that regulates the flow of gas through the manifold and to the second sparging area.

25. The container assembly as recited in claim 24, wherein the first valve and the second valve are electrically operated.

26. The container assembly as recited in claim 24, wherein the first valve and the second valve each comprise a hose clamp.

27. The container assembly as recited in claim 23, further comprising:
a first port coupled with the second polymeric sheet and communicating with the first sparging area; and
a second port coupled with the second polymeric sheet and communicating with the second sparging area.

28. The container assembly as recited in claim 27, wherein the manifold comprises:
a body with a gas inlet port and a plurality of gas outlet ports, the gas inlet port being in fluid communication with each of the plurality of gas outlet ports;
a first gas line extending from the first port to a first one of the plurality of gas outlet ports; and a second gas line extending from the second port to a second one of the plurality of gas outlet ports.

29. The container assembly as recited in claim 22, wherein the first perforations have a different size or number than the second perforations.

30. The container assembly as recited in claim 22, wherein first polymeric sheet and the second polymeric sheet are made of the same material having the same thickness.

31. The container assembly as recited in claim 22, further comprising the bag having a top end wall, the bottom end wall, and an encircling sidewall extending therebetween, the first polymeric sheet or the second polymeric sheet being connected directly to or being integrally formed as a single continuous member with at least a portion of the encircling sidewall.

32. The container assembly as recited in claim 22, the first sparging area being separated from the second sparging area so that a gas entering the first sparging area does not communicate with the second sparging area.

* * * * *